(12) United States Patent
Inami

(10) Patent No.: US 8,549,937 B2
(45) Date of Patent: Oct. 8, 2013

(54) METHOD FOR DETERMINING COP GENERATION FACTORS FOR SINGLE-CRYSTAL SILICON WAFER

(71) Applicant: Shuichi Inami, Tokyo (JP)

(72) Inventor: Shuichi Inami, Tokyo (JP)

(73) Assignee: Sumco Corporation, Tokyo (JP)

( * ) Notice: Subject to any disclaimer, the term of this patent is extended or adjusted under 35 U.S.C. 154(b) by 0 days.

(21) Appl. No.: 13/660,299

(22) Filed: Oct. 25, 2012

(65) Prior Publication Data

US 2013/0054152 A1    Feb. 28, 2013

Related U.S. Application Data

(62) Division of application No. 13/252,311, filed on Oct. 4, 2011, now Pat. No. 8,316,727, which is a division of application No. 12/308,058, filed as application No. PCT/JP2007/060438 on May 22, 2007, now Pat. No. 8,061,225.

(30) Foreign Application Priority Data

Jun. 7, 2006    (JP) ................................. 2006-158488

(51) Int. Cl.
    *G01N 21/88*      (2006.01)

(52) U.S. Cl.
    USPC .............................................. 73/866; 438/16

(58) Field of Classification Search
    USPC .............................................. 73/866; 438/16
    See application file for complete search history.

(56) References Cited

U.S. PATENT DOCUMENTS

| | | | |
|---|---|---|---|
| 5,980,720 A | 11/1999 | Park et al. | |
| 6,392,434 B1 | 5/2002 | Chiu | |
| 6,509,965 B2 | 1/2003 | Fossey | |
| 6,701,029 B1 | 3/2004 | Berfanger et al. | |
| 2002/0054704 A1 | 5/2002 | Smilansky et al. | |
| 2004/0064269 A1* | 4/2004 | Shibuya et al. | 702/40 |
| 2006/0009942 A1 | 1/2006 | Keck et al. | |

FOREIGN PATENT DOCUMENTS

| | | |
|---|---|---|
| DE | 100 48 432 | 5/2001 |
| DE | 101 43 231 | 3/2002 |
| DE | 101 43 761 | 3/2002 |
| JP | 10-227729 | 8/1998 |

(Continued)

OTHER PUBLICATIONS

H. Naruoka et al., "Cu Decoration/SEM ni yoru Kyomen Kenma Kotei Kiln no Sankamaku Taiatsu Furyobu no Kansatsu", Dai 58 Kai Extended abstracts; the Japan Society of Applied Physics, Oct. 1997, p. 242, [2p-N-2].

(Continued)

*Primary Examiner* — Hezron E Williams
*Assistant Examiner* — Paul West
(74) *Attorney, Agent, or Firm* — Clark & Brody

(57) ABSTRACT

A whole determination area of a targeted wafer is concentrically divided in a radial direction, COP density is obtained in each divided determination segment, a maximum value of the COP density is set as COP density$_{RADIUSMAX}$, a minimum value of the COP density is set as COP density$_{RADIUSMIN}$, a value computed by "(COP density$_{RADIUSMAX}$-COP density$_{RADIUSMIN}$)/COP density$_{RADIUSMAX}$" is compared to a predetermined set value, and a non-crystal-induced COP and a crystal-induced COP are distinguished from each other based on a clear criterion, thereby determining the COP generation factor. Therefore, a rejected wafer in which a determination of the crystal-induced COP is made despite being the non-crystal-induced COP can be relieved, so that a wafer production yield can be enhanced.

2 Claims, 4 Drawing Sheets (a)

(b)

(56) References Cited

FOREIGN PATENT DOCUMENTS

| | | |
|---|---|---|
| JP | 2001-081000 | 3/2001 |
| JP | 2002-083853 | 3/2002 |
| JP | 2002-145698 | 5/2002 |
| JP | 2004-193529 | 7/2004 |
| JP | 2005-257576 | 9/2005 |
| JP | 2006-040961 | 2/2006 |
| WO | 02/01626 | 1/2002 |

OTHER PUBLICATIONS

Surfscan SP2 brochure, Copyrigh 2004, KLA-Tencor Corporation.

* cited by examiner (a)

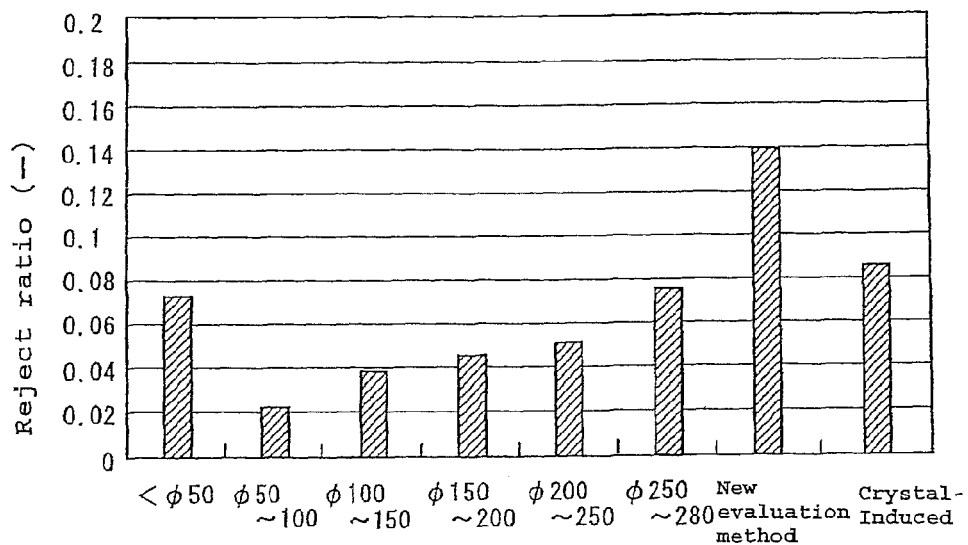

[Criterion]

| | |
|---|---|
| <φ50 | The number of COPs in disc segment of ø50 is more than 10 |
| φ50 ~100 | The number of COPs in ring segment of ø50 to ø100 is more than 23 |
| φ100 ~150 | The number of COPs in ring segment of ø100 to ø150 is more than 13 |
| φ150 ~200 | The number of COPs in ring segment of ø150 to ø200 is more than 17 |
| φ200 ~250 | The number of COPs in ring segment of ø200 to ø250 is more than 21 |
| φ250 ~280 | The number of COPs in ring segment of ø250 to ø280 is more than 16 |
| New evaluation method | Rejected product based on new evaluation method |
| Crystal-Induced | Crystal-induced COPs of rejected products |

METHOD FOR DETERMINING COP GENERATION FACTORS FOR SINGLE-CRYSTAL SILICON WAFER

This application is a divisional application of application Ser. No. 13/252,311, filed on Oct. 4, 2011, which is a divisional application of application Ser. No. 12/308,058, filed on Dec. 5, 2008, now U.S. Pat. No. 8,061,225, which is a national stage application based on PCT/JP2007/060438, filed on May 22, 2007.

TECHNICAL FIELD

The present invention relates to a method for determining COP (Crystal Originated Particle) generation factors aimed at a single-crystal silicon wafer.

BACKGROUND ART

A single-crystal silicon wafer as a semiconductor device substrate is cut out from a single-crystal silicon ingot, and is produced by being subjected to various physical, chemical, and thermal treatments. The single-crystal silicon ingot is usually obtained by the Czochralski method (hereinafter referred to as "CZ method") in which a seed crystal is dipped into silicon melted in a quartz crucible and pulled up to grow a single crystal. However, micro defects called Grown-in defects are induced in the crystal during the single crystal growth.

The Grown-in defects depend on a pulling-up speed during the single crystal growth and a temperature distribution (temperature gradient in crystal in a pulling-up axis-wise direction) in the single crystal immediately after solidification. In the single crystal, the Grown-in defects appear in the form of a hole aggregation defect called COP (Crystal Originated Particles), having sizes ranging from about 0.1 to 0.2 μm, or in the form of a defect including a micro dislocation called a dislocation cluster, being about 10 μm in size.

In the single-crystal silicon wafer produced by the CZ method, an Oxidation-induced Stacking Fault (hereinafter referred to as "OSF") appearing in a ring shape may be generated when the single-crystal silicon wafer is subjected to a high-temperature oxidation heat treatment. A potential area where the OSF ring is generated depends on a thermal history of the crystal during growth, particularly influenced by a pulling-up speed during growth. The region where the OSF ring appears gets shrunk from the outer circumferential side to the inner side of the crystal as the pulling-up speed is lowered.

In other words, the inner side area of the OSF ring spreads to the whole area of wafer when the single crystal is grown at a higher speed, and the outer side area of the OSF ring spreads to the whole area of wafer when the single crystal is grown at a lower speed.

In the case where OSF exists on a wafer surface which is of a device activation area, the OSF causes a leak current to deteriorate a device characteristic. COP is a factor which lowers an initial oxide-film withstand voltage, and the dislocation cluster also causes a defective characteristic of the device formed therein.

Therefore, the single crystal is conventionally grown at a high pulling-up speed such that the ring-shaped OSF generation region is located in the outer circumferential portion of the crystal. For example, as described in Japanese Patent Application Publication No. 2002-145698, there is proposed a wafer in which the OSF region is widely distributed from a circumferential edge portion to a central portion of the wafer and a micro COP region is formed inside the OSF region.

However, a single-crystal silicon wafer (hereinafter referred to as "defect-free crystal silicon wafer") in which the number of Grown-in defects including extremely small COPs is decreased as much as possible is produced with the advance of the fine process of the semiconductor device to cope with growing demand on miniaturization and high performance.

Accordingly, a COP evaluation is made in the defect-free crystal silicon wafer to make an acceptance determination in which crystal integrity (defect-free) is guaranteed by the number of defects (COPs) and the presence or absence of a specific pattern through the COP evaluation. In the COP evaluation, a method called a copper deposition method (copper decoration method) can be employed as an example of the method for detecting COPs.

In the copper deposition method, an uneven insulating film (oxide film) is utilized in a region where the defects (COPs) exist when the oxide film is formed on a wafer surface. After the oxide film having a predetermined thickness is formed on the wafer surface, an external voltage is applied, copper is deposited while the oxide film is destroyed in a defect region on the wafer surface, and the deposited copper is observed to detect the defects (COPs) by the naked eye or with a Transmission Electron Microscope (TEM) or Scanning Electron Microscope (SEM).

The COP generation factors can be classified into the crystal-induced and the non-crystal-induced. The crystal-induced COPs mean the Grown-in defects that are induced into the crystal during the single crystal growth.

According to the investigation thus far, it is found that the generation patterns of the crystal-induced COPs are classified into the following four segments:

(1) The crystal-induced COPs appear in a disc Shape in a central part of wafer.

(2) The crystal-induced COPs appear in a ring shape in an peripheral part of wafer as following its circumference.

(3) The patterns (1) and (2) simultaneously appear, namely, appearing in a disc-ring shape.

(4) The crystal-induced COPs densely appear in the whole surface of the wafer (300 counts or more in a wafer of 300 mm in diameter).

On the other hand, the non-crystal-induced COP is not COP in a strict sense, and caused by a micro flaw or scratch generated on the wafer surface during handling the silicon wafer. When the non-crystal-induced COPs are observed with a surface defect inspection apparatus (for example, SP2: product of KLA-Tencor) or by the copper deposition method (copper decoration method), the COPs are generated in a line shape, or in a dot shape locally or in the whole surface of the wafer.

Since the non-crystal-induced COP is not an intrinsic defect derived from the silicon single crystal itself, which is a constituent of a wafer, the non-crystal-induced COPs should be removed from the COP evaluation object. In the current COP evaluation, COPs which are easily determined as the non-crystal-induced are removed from the evaluation.

However, there is no proper method for distinguishing the non-crystal-induced COP and the crystal-induced COP from each other (that is, both are identified to thereby allow the non-crystal-induced COPs to be excluded in the evaluation), in particular, there is no method for determining that the non-crystal-induced COPs appearing in a dot shape in the whole surface of the wafer are irrelevant to crystal-induced COPs.

DISCLOSURE OF THE INVENTION

As described above, the COP evaluation has been carried out in the defect-free crystal silicon wafer. However, unfortunately the non-crystal-induced COPs which should be ruled out in the COP evaluation, particularly plain COPs appearing in a dot shape in the whole surface of the wafer are hardly distinguished from the crystal-induced COPs.

That is, determining plain COPs generated in a line shape or plain COPs locally generated in a dot shape as being non-crystal-induced is easily made. However, in the case where cover-whole-surface COPs as being generated in a dot, shape in the whole surface of the wafer, determining whether the COPs are crystal-induced or non-crystal-induced is really difficult, while it is just left to an operator who is technically educated how to determine. Even if COPs are generated, the wafer should be acceptable so long as the COPs appear as being non-crystal-induced. Therefore, when such acceptable wafers should be rejected as being non-acceptable, a wafer production yield is unduly lowered.

Clarifying a criterion for a generation factor of such COPs appearing in a dot shape in the whole surface of the wafer can be cited as one of means for enhancing accuracy of the acceptance determination. However, since the determination depends on the judgment by human eyes (visual inspection), it is difficult to delineate the criterion in words.

In the event when a production amount may increase from now, in order that the supply of the stable-quality wafer is realized while the production yield is enhanced, it is necessary to clarify the criterion for the non-crystal-induced COPs, in other words, to quantitatively define the criterion by a numerical value. The clear criterion is also necessary to automate the COP evaluation (inspection).

In view of the foregoing, an object of the present invention is to provide a quantitative method for determining COP generation factors for a single-crystal silicon wafer, in which the non-crystal-induced COP and the crystal-induced COP are distinguished from each other based on a clear criterion in order to properly make the COP evaluation.

The present inventor makes investigations in order to solve the above problem to establish the method capable of identifying COP generation factors based on the clear criterion. As a result, the present inventor devises a method, in which the feature of the after-mentioned crystal-induced COP generation behavior is utilized to check a density distribution obtained by computing the COP density in an r-direction (radial direction) or a θ-direction (circumferential direction) of the wafer against a threshold value set by a semi-empirical technique, or to consider a COP generation position, thereby determining whether COPs are either crystal-induced or non-crystal-induced.

The summary of the present invention includes the following methods (1) to (4) for making a COP evaluation on a single-crystal silicon wafer.

(1) A method for determining COP generation factors for a single-crystal silicon wafer, in which a determination area of the wafer is concentrically divided into segments in a radial direction, COP density is obtained by enumerating in each divided determination segment, a maximum value of the COP density is set as COP density$_{RADIUSMAX}$, a minimum value of the COP density is set as COP density$_{RADIUSMIN}$, and determination that the COP generation factor is the one other than a defect induced during crystal growth is made when a value computed by "(COP density$_{RADIUSMAX}$-COP density$_{RADIUSMIN}$)/COP density$_{RADIUSMAX}$" is not more than a predetermined set value.

(2) A method for determining COP generation factors for a single-crystal silicon wafer, in which a determination area of the wafer is concentrically divided into segments in a radial direction, and determination that COPs generated in segments other than a central segment and an outer circumferential segment among divided determination segments are attributed to a factor other than a defect induced during crystal growth is made.

In the methods for determining the COP generation factors for the single-crystal silicon wafer according to the above (1) or (2), a width of each concentrically-divided determination segment desirably ranges from 15 mm to 30 mm.

(3) A method for determining COP generation factors for a single-crystal silicon wafer, in which a determination area of the wafer is concentrically divided in a radial direction and further circumferentially divided into segments, COP density of each concentrically-circumferentially-divided determination segment within the area of a concentrically-divided primary segment is obtained and assessed on the same radius basis, wherein a maximum value among determination segments for each circumferentially-divided primary segment is set as COP density$_{CIRCUMFERENCEMAX}$, likewise a minimum value as COP density$_{CIRCUMFERENCEMIN}$, and determination is made such that the COP generation is attributed to a factor other than a defect induced during crystal growth, when a value computed by "(COP density$_{CIRCUMFERENCEMAX}$-COP density$_{CIRCUMFERENCEMIN}$)/COP density$_{CIRCUMFERENCEMAX}$" is not less than a predetermined set value.

In the method for determining COP generation factors for a single-crystal silicon wafer according to the above (3), a width of each concentrically-divided segment desirably ranges from 15 mm to 30 mm, and each concentrically-divided primary segment is further circumferentially divided into three to eight determination segments.

(4) A method for determining COP generation factors for a single-crystal silicon wafer, in which determination is made such that the COP generation is attributed to a factor other than a defect induced during crystal growth, when COPs are generated in a line shape, in a dotted-line shape or in a dot shape locally.

In the methods for determining COP generation factors for a single-crystal silicon wafer according to the above (1) to (4), the "single-crystal silicon wafer" is mainly directed to a silicon wafer of 300 mm in diameter. That is, the evaluation method according to the present invention is mainly aimed at a large-diameter silicon wafer having a diameter of 300 mm or more.

In the method for determining COP generation factors for a single-crystal silicon wafer of the present invention, the determination area of the wafer is concentrically divided in a radial direction or further circumferentially divided, and the non-crystal-induced COP and the crystal-induced COP are distinguished from each other based on COP density obtained in each determination divided segment or in consideration of COP generation position. In the determination method of the present invention, the determination of the COP generation factor can be made based on the clear criterion.

According to the method of the present invention, the rejected wafer in which the determination as the crystal-induced COP had been made irrespective of non-crystal-induced can be relieved/rescued (accepted) to thereby enhance the wafer production yield. The clear criterion can provide the stable-quality wafer.

BRIEF DESCRIPTION OF THE DRAWINGS

FIG. 4 is a chart showing a COP evaluation result of the single-crystal silicon wafer in the COPs evaluation process.

BEST MODES FOR CARRYING OUT THE INVENTION

The methods for determining COP generation factors for a single-crystal silicon wafer according to the above (1) to (4) of the invention will be specifically described below. In the targeted COPs of the present invention, the number of COPs and their distribution are visually inspected on the wafer surface using a surface defect inspection apparatus (for example, SP1: product of KLA-Tencor).

Generally, the crystal-induced COPs appear in a disc shape, ring shape, or disc-ring shape. The crystal-induced COPs may also appear in high density in the whole surface of the wafer. The reason why COPs appear in such patterns is that the following particular relationship holds between a pulling-up speed and a distribution of the Grown-in defects induced during the single-crystal growth when a seed crystal is dipped in silicon melt in a quartz crucible and pulled up.

Figure 1:
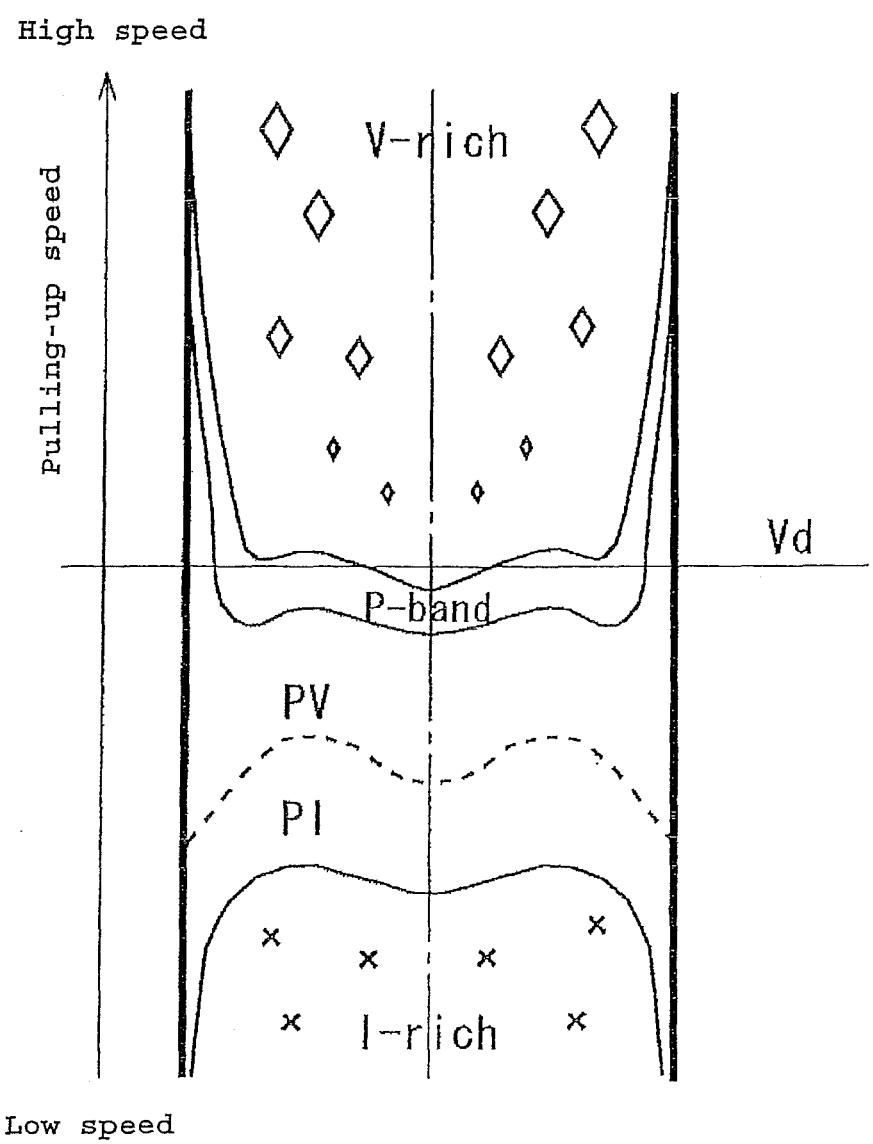
FIG. 1 is a view schematically showing an example of a Grown-in defect distribution state.

FIG. 1 is a view schematically showing an example of a defect distribution state of a section of a silicon single crystal pulled up by a growth apparatus which can produce a wafer having an extremely small amount of Grown-in defects, while the defect distribution state is contrasted with the pulling-up speed. FIG. 1 shows the observation result of the micro-defect distribution state in which a grown single crystal is cut along a pulling-up axis, the cut single crystal is dipped in a copper nitrate solution to deposit Cu, and the micro defects are observed by X-ray topography after heat treatment.

In FIG. 1, "V-rich" means an area where the number of COPs is increased, and "I-rich" means an area where a number of dislocation cluster defects caused by trapped interstitial atoms during the single-crystal growth exist. "P-band" means an Oxygen-induced Stacking Fault (OSF). "PV" located on a lower pulling-up speed side of the "P-band" is an oxygen precipitation promotion region which is of a defect-free region where vacancies are dominant, and "PI" located on a further lower pulling-up speed side of the "PV" is an oxygen precipitation suppression region which is of a defect-free region where the interstitial atoms are dominant.

In the case where the single crystal is pulled up at a pulling-up speed corresponding to the defect-free region, the wafer having an extremely small amount of Grown-in defects is obtained. However, in the case where the pulling-up speed is shifted toward the higher-speed side, COPs having a specific pattern are generated. For example, in the case where a cross section of the silicon single crystal has the defect distribution state shown in FIG. 1, the wafer in which COPs in a disc-shaped pattern exist in the central portion is obtained when the single crystal is pulled up at a pulling-up speed Vd.

Depending on a thermal history in a pulling furnace, an in-plane distribution of the defects (LPD, OSF) on the V-rich side can have a configuration in which the central portion is stretched toward the low-speed side or a configuration in which the outer circumferential portion is stretched toward the low-speed side, in addition to the configuration as shown in FIG. 1 in which the central portion and the outer circumferential portion are substantially evenly stretched toward the low-speed side. However, assuming that r designates a radius, a portion having about r/2 (that is, a distance of about ½ from the center in a radial direction) cannot be stretched toward the low-speed side. Accordingly, the crystal-induced COPs should have a disc-shaped pattern and/or a ring-shaped pattern. In particular, the ring-shaped pattern is not generated at a position near r/2, but is generated in a manner to follow the outer circumference of the crystal.

Since the thermal history is symmetric about the axis (pulling-up axis), COPs are evenly generated also in a θ-direction (circumferential direction of the wafer). Accordingly, density of COPs generated in a ring shape or disc shape is substantially uniform in a circumferential direction.

COPs appear in dense in the whole surface of the wafer when the pulling-up speed is largely shifted toward the high-speed side. In such a case, the COP density becomes high, and the number of COPs is not less than 300-400 in the whole surface of the wafer. Accordingly, even if the COPs should appear in the whole surface of the wafer, when the number of COPs is not more than about 200, it is considered that the COP generation factor is not crystal-induced.

The crystal-induced COPs exhibit such a generation behavior as described above. The method for determining a COP generation factor according to the present invention utilizes the generation behavior to determine whether COPs are crystal-induced or non-crystal-induced.

The determination method (1) of the present invention is aimed at the single-crystal silicon wafer having extremely small amount of Grown-in defects. In the method (1), the determination area of the wafer is concentrically divided into segments in a radial direction, the COP density is obtained in each divided determination segment, and the determination that the COP generation factor is attributed to a factor other than the defect induced during crystal growth is made when the value computed by "(COP density$_{RADIUSMAX}$-COP density$_{RADIUSMIN}$)/COP density$_{RADIUSMAX}$" is not more than a predetermined set value. As used herein, COP density$_{RADIUSMAX}$ means a maximum value of the COP density obtained in each divided determination segment, and COP density$_{RADIUSMIN}$ does a minimum value likewise.

The determination method (1) is the one which focuses on a COP density distribution in an r-direction (radial direction of the wafer). The value of "(COP density$_{RADIUSMAX}$-COP density$_{RADIUSMIN}$)/COP density$_{RADIUSMAX}$" (hereinafter referred to as "evaluation function") computed by obtaining the COP density in each divided determination segment is an index indicating whether or not the COP distribution is even. When the evaluation function has a small value, it can be said that a difference in COP density between the divided determination segments is small and the COP distribution is even in an r-direction on the wafer surface.

As described above, since the crystal-induced COPs have a disc-shaped pattern or a ring-shaped pattern, the COP distribution is not even in an r-direction and the evaluation function "(COP density$_{RADIUSMAX}$-COP density$_{RADIUSMIN}$)/COP density$_{RADIUSMAX}$" has a large value when the crystal-induced COPs are generated. Accordingly, when the value of the evaluation function "(COP density$_{RADIUSMAX}$-COP density$_{RADIUSMIN}$)/COP density$_{RADIUSMAX}$" is not more than a predetermined set value, COPs can be regarded as not having a disc-shaped pattern and/or a ring-shaped pattern, and it can be determined that the COP generation is attributed to the factor other than the defect induced during the crystal growth; (that is, non-crystal-induced COPs).

The set value is determined in a semi-empirical fashion based on actual results in the conventional determination.

In the determination method (2), the determination area of the wafer is concentrically divided into segments in a radial direction, and determination is made such that COPs generated in segments other than the central segment and the outer circumferential segment among divided determination segments are attributed to the factor other than the defect induced during the crystal growth.

The determination method (2) focuses on COP generation positions in a r-direction. The crystal-induced COPs have a disc-shaped pattern or a ring-shaped pattern, and are not generated in segments other than the central and outer circumferential segments of the wafer, so that the COPs generated in the segments other than the central and outer circumferential segments can be regarded as the non-crystal-induced COPs.

In the determination method (1) or (2), the width of each concentrically-divided determination segment (i.e., ring) desirably ranges from 15 mm to 30 mm.

The determination methods are mainly aimed at the wafer having a diameter of 300 mm. Generally, since the ring-shaped segment of the outermost circumference having a width of 10 mm is ruled out from evaluation, assuming that the wafer has a diameter of 300 mm, the determination segment pertinent to evaluation ranges from the center of the wafer to a radius of 140 mm. In the case where the area ranging from the center of the wafer to the radius of 140 mm is divided into ring shape segments, when the width of the ring is narrower than 15 mm, the number of determination segments is excessively increased to complicate the evaluation, which leads to cost increase.

When the width of the ring segment is wider than 30 mm, the evaluation becomes coarse to lose accuracy of the evaluation. Therefore, the width of about 25 mm is suitable to the wafer having a diameter of 300 mm. Each determination segment is preferably evenly divided to have an even width, but necessarily limited to it, and the width may be flexibly defined as appropriate based on the COP generation condition and the like.

In the determination method (3), the determination area of the wafer is concentrically divided in a radial direction to primary segments and further circumferentially divided to determination segments, i.e., relevant segments, the COP density of each concentrically circumferentially divided determination segment, i.e., relevant segment, is obtained and assessed within each primary segment that is defined by concentrically dividing the whole determination area of the wafer, a maximum value in a primary segment of the same radius is set as COP density$_{CIRCUMFERENCEMAX}$, a minimum value is set as COP density$_{CIRCUMFERENCEMIN}$, and determination is made such that the COP generation factor is attributed to the factor other than the defect induced during the crystal growth, when the value computed by "(COP density$_{CIRCUMFERENCEMAX}$−COP density$_{CIRCUMFERENCEMIN}$)/COP density$_{CIRCUMFERENCEMAX}$" is not less than a predetermined set value. As used herein, the COP density$_{CIRCUMFERENCEMAX}$ means a maximum value of the COP density obtained among relevant determination segments within a primary segment of the same radius, and the COP density$_{CIRCUMFERENCEMIN}$ means a minimum value likewise.

The determination method (3) focuses on a COP distribution behavior in a θ-direction (circumferential direction of the wafer). As described above, since the thermal history of the grown single crystal is symmetric about the axis of pulling-up, COPs are evenly generated in a θ-direction, and the density of COPs generated in a ring shape pattern or disc shape pattern is substantially uniform in a θ-direction.

Accordingly, in the determination method (3), the whole determination area of the wafer is concentrically divided in a radial direction to primary segments and further circumferentially divided to relevant determination segments, and the COP density of each relevant determination segment is obtained and assessed within each primary segment of the same radius as defined above. When the value of the evaluation function "(COP density$_{CIRCUMFERENCEMAX}$−COP density$_{CIRCUMFERENCEMIN}$)/COP density$_{CIRCUMFERENCEMAX}$" is not less than the predetermined set value, determination is made such that the COP generation factor is non-crystal-induced since the COP density of each relevant determination segment in a circumferential direction is not uniform.

In the determination method (3), a width of each concentrically-divided primary segment (i.e., ring) desirably ranges from 15 mm to 30 mm, and each primary segment is circumferentially divided into three to eight relevant determination segments.

The reason why the width of each concentrically-divided primary segment, a ring, ranges from 15 mm to 30 mm is already described as above. The reason why each ring is circumferentially divided into three to eight relevant determination segments is as follows. The determination accuracy is not enhanced too much even if the number of relevant determination segments divided in a circumferential direction is excessively increased. When the ring is divided into two segments, since the relevant determination segment is excessively wide in a θ-direction, the change in COP density does not appear prominently even if the COP distribution density varies in a θ-direction, which lowers the determination accuracy.

In the determination method (4), determination is made such that the COP generation factor is attributed to the factor other than the defect induced during the crystal growth, when COPs are generated in a line shape, in a dotted-line shape or in a dot shape locally.

COPs generated in a line shape, in a dotted-line shape or in a dot shape locally are clearly attributed to the micro flaw and scratch generated on the sample surface, so that these COPs can be easily determined as being non-crystal-induced. Accordingly, such COPs are ruled out from determination.

The result of the determination, in which the COP generation factor is determined based on the determination method of the present invention to investigate whether or not the determination method can be applied, will be described below.

The following methods (a) to (e) are used in the determination. The methods (a) to (c) (a determination method (1)) focus on the COP density distribution in an r-direction of the wafer, the method (d) (a determination method (2)) focus on the COP generation position in an r-direction, and the method (e) (a determination method (3)) focus on the COP distribution behavior in a θ-direction of the wafer.

(a) The method in which the determination of the non-crystal-induced COP is made when the COP density distribution is uniform in the range of ϕ50 to ϕ250

A ring-shaped area of ϕ50 to ϕ250 is divided into plural segments in an r-direction, the value of the evaluation function "(COP density$_{RADIUSMAX}$−COP density$_{RADIUSMIN}$)/COP density$_{RADIUSMAX}$" is obtained in each determination segment, and the determination of non-crystal-induced COP is made when the value is not more than the predetermined set value (threshold). The range of "ϕ40-ϕ250" indicates a ring-shaped area between circles of 50 mm and 250 mm in diameter.

(b) The method in which the determination of the non-crystal-induced COP is made when the COP density distribution is uniform in the range of ϕ100 to ϕ250

In the method (b), the COP observation position is changed from that of the method (a), and others are identical to those of the method (a).

(c) The method in which for a rejected wafer by a COP evaluation method, the determination whether or not COPs in the rejected area are non-crystal-induced is made based on the COP density distribution.

The above COP evaluation method is used to make the acceptance determination whether or not the crystal integrity (defect-free) is guaranteed by the number of COPs and the presence or absence of a specific pattern. In the COP evaluation method proposed herein by the present inventor, the whole determination area of the wafer is concentrically divided in a radial direction to segments, an upper limit value of the number of COPs is set in each divided determination segment, and the acceptance determination is made based on the upper limit value. This method is referred to as "new evaluation method".

The determination segment where the rejection as non-acceptable is made (hereinafter referred to as "NG"), that is, the determination segments where the number of COPs exceeds the reference value are extracted in each rejected wafer by the "new evaluation method", and the COP density is computed. The value of the evaluation function "(COP density$_{RADIUSMAX}$-COP density$_{RADIUSMIN}$)/COP density$_{RADIUSMAX}$" is obtained only for the extracted determination segments, and the determination of the non-crystal-induced COP is made when the value of the evaluation function is not more than the predetermined set value (threshold). However, in the case of only one segment where the number of COPs exceeds the reference value, the COP density$_{RADIUSMIN}$ is set to 0, and the value of evaluation function is set to 1.

(d) The method in which the determination whether or not COPs are non-crystal-induced is made based on the COP generation position It is assumed that COPs generated in the range of $\phi$50 to $\phi$200 are the non-crystal-induced COPs.

(e) The method in which the determination of the non-crystal-induced COP is made, for the rejected wafer by the new evaluation method, when the COP density distribution is not uniform in a θ-direction of the wafer The wafer is divided into first to fourth quadrant, the COP density is obtained from the number of COPs counted in each quadrant, and the determination of the non-crystal-induced COP is made when the value computed by the evaluation function "(COP density$_{CIRCUMFERENCEMAX}$-COPdensity$_{CIRCUMFERENCEMIN}$)/ COPdensity$_{CIRCUMFERENCEMAX}$" in the relevant determination segments within a primary segment of the identical radius is not less than the predetermined set value (threshold).

Table 1 shows the determination result obtained by the methods (a) and (b). The determination of the non-crystal-induced dot-shaped COP is made by the visual inspection for nine wafers (samples) used as the determination object (also shown in Table 1 as a reference). The threshold is changed in two levels for both the methods (a) and (b), and the determination is made on four conditions in total.

TABLE 1

| | Determination method | | | | |
|---|---|---|---|---|---|
| | Visual determination (reference) | (a) Determination based on COP density distribution in $\phi$50-$\phi$200 | | (b) Determination based on COP density distribution in $\phi$100-$\phi$250 | |
| Threshold | — | 0.5 | 0.7 | 0.5 | 0.7 |
| The number of determinations | 9 | 7 | 7 | 7 | 8 |

As shown in Table 1, for the nine samples in which the determination of the non-crystal-induced dot-shaped COP is made by the visual inspection, the determination of the non-crystal-induced dot-shaped COP can be made for seven samples by the determination method (a), and for seven or eight samples by the determination method (b).

Figure 2:
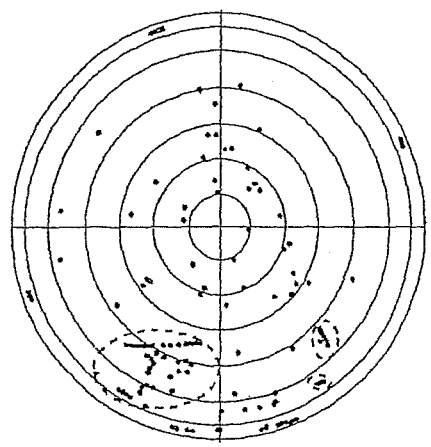
FIGS. 2(a) and 2(b) are views showing COPs in samples where determination as non-crystal-induced COPs could not be made at an earlier stage of an investigation on a method for determining COP generation factors.
Figure 2:
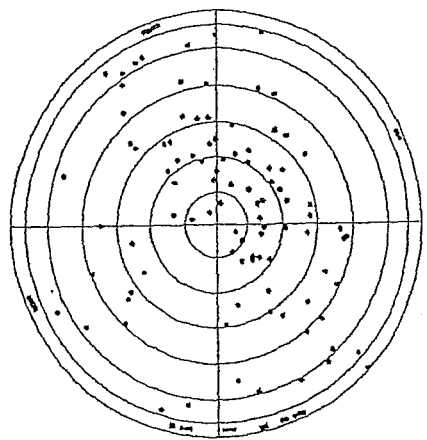

FIGS. 2(a) and 2(b) are views showing COPs in the samples where the determination of the non-crystal-induced COP cannot be made by the determination method (a) or (b), in which FIG. 2(a) shows the sample where the determination of the non-crystal-induced COP cannot be made on the four conditions in the determination methods (a) and (b), and FIG. 2(b) shows the sample where the determination of the non-crystal-induced COP can be made in the case where the threshold is set to 0.7 in the determination method (b) while the determination of the non-crystal-induced COP cannot be made in the remaining three conditions. In FIG. 2(a), a portion surrounded by a broken-line ellipse indicates the linearly-generated non-crystal-induced COPs.

Table 2 shows the determination result obtained by the methods (c) and (d). The same nine samples as the determination method (a) or (b) are used in the methods (c) and (d).

TABLE 2

| | Determination method | |
|---|---|---|
| | (c) Determination based on COP density distribution in NG portion | (d) Determination based on COP generation position in NG portion |
| Threshold | 0.8 | — |
| The number of determinations | 8 | 3 |

In the determination method (c), as described above, for the rejected samples by the new evaluation method, the value of the evaluation function "(COP density$_{RADIUSMAX}$-COP density$_{RADIUSMIN}$)/COP density$_{RADIUSMAX}$" is obtained for only the segment where the number of COPs exceeds the reference value to become NG, and the determination of the non-crystal-induced is made when the value of the evaluation function is not more than 0.8. In the determination method (c), the determination of the non-crystal-induced can be made for the eight samples of the nine non-crystal-induced samples.

The determination method (d) is one in which the determination of the non-crystal-induced is made for COPs generated in the range of $\phi$50 to $\phi$200. In the determination method (d), the determination of the non-crystal-induced can be made for the three samples of the nine samples in which the non-crystal-induced COPs are generated.

The determination method (e) in which the determination of the non-crystal-induced COP is made by the distribution behavior in the e-direction is applied to the same nine samples as the determination method (a) or (b). That is, each determination area divided in the ring shape is divided into the first to fourth quadrants, the evaluation function "(COP density$_{CIRCUMFERENCEMAX}$-COP density$_{CIRCUMFERENCEMIN}$)/COP density$_{CIRCUMFERENCEMAX}$" is computed between the quadrants in the same primary, ring segment, the threshold is set to 0.8, and the determination that COPs generated in the wafer are non-crystal-induced is made when the relationship of "(COP density$_{CIRCUMFERENCEMAX}$-COP density$_{CIRCUMFERENCEMIN}$)/COP density$_{CIRCUMFERENCEMAX}$">0.8 holds in all the ring segments.

As a result, the determination of the non-crystal-induced COP can be made for only one sample.

Accordingly, the determination method (e) is not suitable to the method for determining the non-crystal factor to the sample in which the non-crystal-induced COPs are generated. Thus, an example application of the method for determining COP generation factors of the present invention is described.

The determination method (e), that is, the method described in (3) in which the determination of the non-crystal-induced COP is made based on the distribution behavior in a θ-direction is not suitable to the determination method for the samples used in the example of application. However, as described below, the determination method (e) does not lose significance as the method for determining COP generation factors of the present invention.

When the determination methods (1) to (3) are actually applied, it is necessary that, in consideration of the COP generation (existence) state in the produced wafer and a quality level required for the wafer, the semi-empirical technique of utilizing the actual results of the past COP generation factor determination be taken to define a specific criterion such as the width of the divided determination segment and a setting value (threshold).

Accordingly, the determination method (3) can be established as the sufficiently applicable determination method by finding the more proper condition for the specific criterion.

In applying the method for determining COP generation factors of the present invention to the COP evaluation of the single-crystal silicon wafer, obviously the method of the present invention can be solely applied, the determination of the COP generation factor is made based on the clear criterion, and the non-crystal-induced COP can be distinguished from the crystal-induced COP (ruled out from the COP evaluation). However, the determination method of the present invention can be more effectively utilized to enhance the COP evaluation accuracy and reliability of the single-crystal silicon wafer by a combination with the conventional COP evaluation method of the single-crystal silicon wafer, desirably the improved COP evaluation method.

A system (process) for evaluating COPs of the single-crystal silicon wafer, in which the method for evaluating COP generation factors of the present invention is combined with the "new evaluation method", will be described below. The COP evaluation process is based on the result of the investigation whether or not the above-described determination method of the present invention is applicable. For example, when the wafer to be evaluated is changed due to the change in production condition, since the COP generation (existence) state is changed in the wafer, more proper setting may be required for the width of the divided determination segment or the threshold.

In the process for evaluating COPs of the single-crystal silicon wafer, in which the method, for determining COP generation factors of the present invention is incorporated, the procedure (process) is as follows.

The procedure 1: The determination is made based on the number of COPs in the whole surface of the wafer. The determination is made for the acceptable wafer by the "new evaluation method" of procedure 2. The rejected wafer is transferred to the procedure 3.

The procedure 2: The acceptance determination of the silicon wafer is made by the "new evaluation method". The pattern determination is made in the acceptance determination of the procedure 2.

The procedure 3: For the rejected wafer in the procedures 1 and 2 (particularly, the number of COPs exceeds the reference value, and therefore the total number of COPs exceeds the reference value), based on the COP density distribution, the determination whether or not COPs are non-crystal-induced is made. For example, the method (a) for determining COP generation factors is performed with the setting value (threshold) of 0.7. The final determination is visually made for the acceptable wafer in the procedure 3.

The procedure 4: For the rejected wafer in the procedure 3, based on the COP generation position, the determination whether or not COPs are non-crystal-induced is made. For example, the method (d) for determining COP generation factors is performed with the setting value (threshold) of 0.8. The final determination is visually made for the acceptable wafer in the procedure 4.

Since the initial application of the COP evaluation process is a test operation, the visual determination is made in the procedures 3 and 4 to confirm adequacy of the width of the divided determination segment of the wafer and the setting value (threshold).

Figure 3:
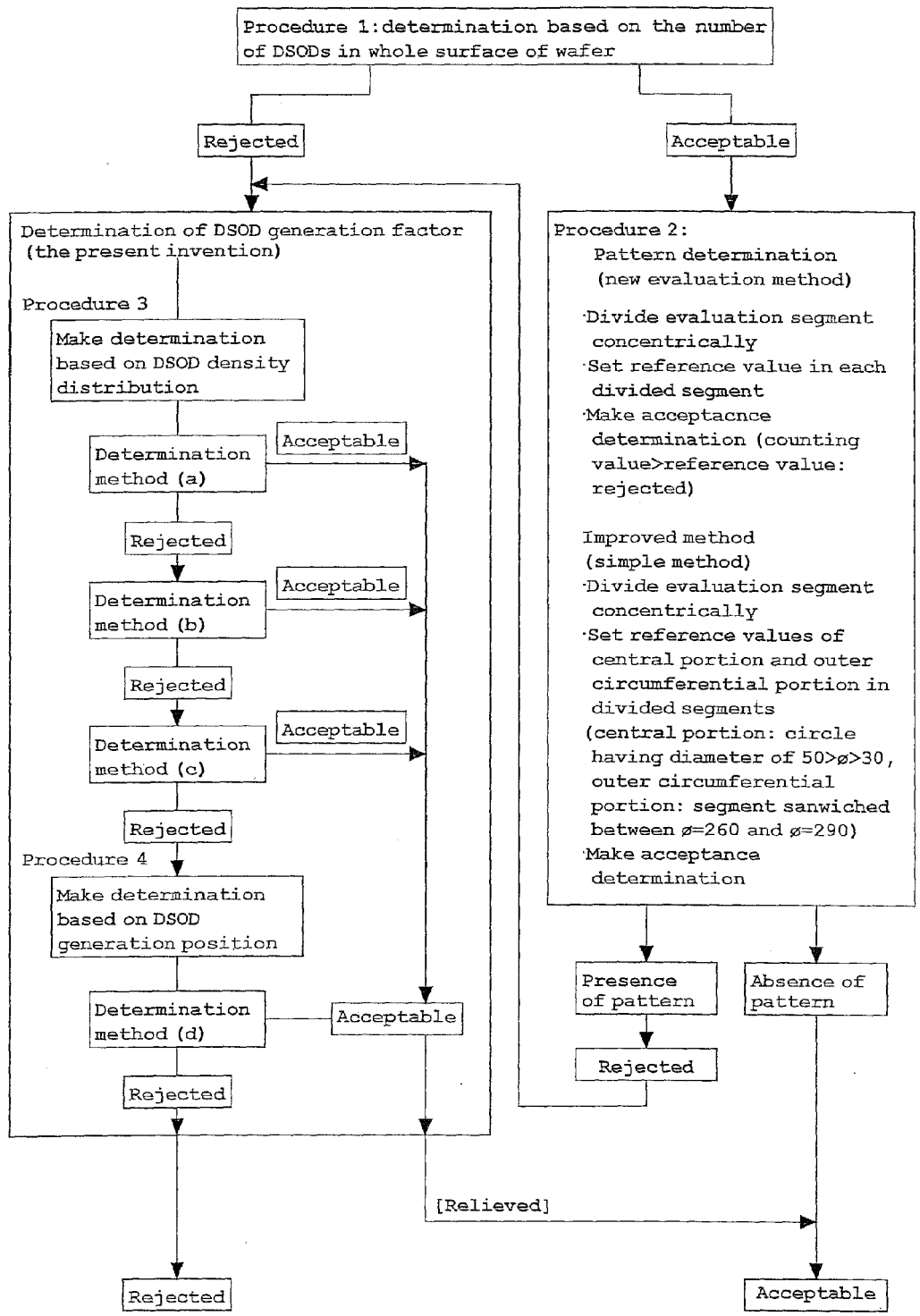
FIG. 3 is a chart showing a process of evaluating COPs on a single-crystal silicon wafer.

FIG. 3 is a chart schematically showing a process of evaluating COPs of the single-crystal silicon wafer. The "procedure 1" to "procedure 4" and the methods (a) to (d) of the procedures 3 and 4 in the FIG. 3 correspond to the "procedure 1" to "procedure 4" and the methods (a) to (d) described above. The "acceptable" and "rejected" surrounded by solid-line frames indicate acceptable and rejected in a mid-flow stage of the COP evaluation, and the "acceptable" and "rejected" surrounded by double solid lines indicate final result of the COP evaluation.

As shown in FIG. 3, when the method for determining a COP generation factor of the present invention is combined with the "new evaluation method", the rejected wafer in the COP total number determination (procedure 1) or the rejected wafer in the pattern determination (procedure 2) are relieved due to the determination of the non-crystal-induced COP (see an arrow shown by a bold solid line), so that the wafer production yield can be enhanced.

FIG. 4 is a chart showing a COP evaluation result of the single-crystal silicon wafer performed by the above process of evaluating COPs. In FIG. 4, the process of evaluating COPs is applied to the defect-free crystal silicon wafer (n=173).

In the horizontal axis of FIG. 4, "<φ50" means a disc-shaped segment having a diameter of lower than 50 mm, and "φ50-φ100" means a ring-shaped segment having a diameter of 50 mm to 100 mm. In each of the determination segments from "<φ50" to "φ250-φ280", the reject ratio is a ratio of the rejected wafer based on each of the criteria shown in the lower portion of FIG. 4 to the total number of wafers, and the reject ratio in each determination segment includes the overlapping wafer.

The reject ratio in the "new evaluation method" of the horizontal axis indicates the total number (excluding the overlapping) of the rejected wafers based on each of the criteria. The reject ratio in the "crystal-induced" is a reject ratio, in which the determination method of the present invention incorporated in the COP evaluation process is applied to distinguish the non-crystal-induced COP and the crystal-induced COP from each other, and the wafer in which the determination of the non-crystal-induced COP is made is removed from the rejected wafer the "new evaluation method" of the horizontal axis.

As can be seen from FIG. 4, when the determination method of the present invention is applied, the reject ratio is decreased from 0.139 to 0.087, thereby enhancing the wafer production yield.

INDUSTRIAL APPLICABILITY

In the method for determining COP generation factors for a single-crystal silicon wafer according to the present invention, the non-crystal-induced COP and the crystal-induced COP are distinguished from each other based on the clear criterion to determine the COP generation factors. According to this method, the rejected wafer in which the determination of the crystal-induced COP is made despite being non-crystal-induced COP can be relieved, so that the wafer production yield can be enhanced.

Accordingly, the method for determining a COP generation factor of the present invention can be suitably applied to the production of the single-crystal silicon wafer and the production of the semiconductor device.

The invention claimed is:

1. A method for determining a COP generation factor of a single-crystal silicon wafer, wherein a determination area of the wafer is concentrically divided in a radial direction, and a determination that COPs generated in segments except for a central portion and an outer circumferential portion in the divided determination segments are attributed to a factor except for a defect induced during crystal growth is made.

2. The method for determining a COP generation factor of a single-crystal silicon wafer according to claim 1, wherein a width of each concentrically-divided determination segment ranges from 15 mm to 30 mm.

* * * * *